(12) United States Patent
Roberts et al.

(10) Patent No.: US 11,246,993 B2
(45) Date of Patent: Feb. 15, 2022

(54) SAFETY DEVICE FOR A PRE-FILLED SYRINGE AND AN INJECTION DEVICE

(71) Applicant: Sanofi-Aventis Deutschland GMBH, Frankfurt am Main (DE)

(72) Inventors: Gareth Roberts, Wrexham (GB); John Slemmen, Mereyside (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 146 days.

(21) Appl. No.: 16/139,823

(22) Filed: Sep. 24, 2018

(65) Prior Publication Data

US 2019/0022334 A1 Jan. 24, 2019

Related U.S. Application Data

(63) Continuation of application No. 15/165,624, filed on May 26, 2016, now Pat. No. 10,080,847, which is a (Continued)

(30) Foreign Application Priority Data

Jan. 4, 2011 (EP) .................................... 11150080

(51) Int. Cl.
 *A61M 5/32* (2006.01)
 *A61M 5/20* (2006.01)

(52) U.S. Cl.
 CPC .......... *A61M 5/3202* (2013.01); *A61M 5/326* (2013.01); *A61M 5/3213* (2013.01); (Continued)

(58) Field of Classification Search
 CPC .. A61M 2005/2073; A61M 2005/3223; A61M 2005/3247; A61M 2005/3267; (Continued)

(56) References Cited

U.S. PATENT DOCUMENTS

| 6,939,330 B1 | 9/2005 | McConnell-Montalvo et al. |
| 2005/0033230 A1* | 2/2005 | Alchas .................. A61M 5/326 604/117 |

(Continued)

FOREIGN PATENT DOCUMENTS

| CN | 1713930 | 12/2005 |
| CN | 101287512 | 10/2008 |

(Continued)

OTHER PUBLICATIONS

Chinese Office Action in Patent Application No. 201180068983.7, dated Nov. 2, 2015, 2 pages (English translation).
(Continued)

*Primary Examiner* — Rebecca E Eisenberg
(74) *Attorney, Agent, or Firm* — Fish & Richardson P.C.

(57) ABSTRACT

According to the invention, a safety device for a pre-filled syringe with an injection needle comprises of a support body adapted to mount the pre-filled syringe, a needle shield slidably arranged with respect to the support body, a retention and locking means (M) for retaining and locking the needle shield with respect to the support body in a first and a second advanced position (PA1, PA2) and in a retracted position (PR). The needle shield comprises an annular flange adapted to rest on the skin of the patient receiving an injection. The retention and locking means (M) are arranged at a distal end of the safety device.

23 Claims, 17 Drawing Sheets

Related U.S. Application Data continuation of application No. 13/997,370, filed as application No. PCT/EP2011/074277 on Dec. 30, 2011, now Pat. No. 9,352,101.

(52) U.S. Cl.
CPC ........ *A61M 5/3245* (2013.01); *A61M 5/3287* (2013.01); *A61M 5/20* (2013.01); *A61M 2005/2073* (2013.01); *A61M 2005/3223* (2013.01); *A61M 2005/3247* (2013.01); *A61M 2005/3267* (2013.01); *A61M 2205/583* (2013.01); *A61M 2205/59* (2013.01)

(58) Field of Classification Search
CPC .... A61M 5/20; A61M 5/3202; A61M 5/3245; A61M 5/326; A61M 5/3287
See application file for complete search history.

(56) References Cited

U.S. PATENT DOCUMENTS

| | | | |
|---|---|---|---|
| 2009/0024093 | A1 | 1/2009 | Carrel et al. |
| 2010/0049125 | A1 | 2/2010 | James et al. |
| 2013/0211338 | A1* | 8/2013 | Roberts ............... A61M 5/3287 604/198 |
| 2013/0281939 | A1 | 10/2013 | Roberts et al. |

FOREIGN PATENT DOCUMENTS

| | | |
|---|---|---|
| CN | 101854967 | 10/2010 |
| EP | 1970086 | 9/2008 |
| EP | 2060292 | 5/2009 |
| FR | 2884721 | 10/2006 |
| FR | 2884722 | 10/2006 |
| FR | 2899482 | 10/2007 |
| JP | 2007-511285 | 5/2007 |
| JP | 2008-518678 | 6/2008 |
| JP | 2008-536598 | 9/2008 |
| WO | WO 2001/085239 | 11/2001 |
| WO | WO 2004/007892 | 1/2004 |
| WO | WO 2004/047892 | 6/2004 |
| WO | WO 2005/113039 | 12/2005 |
| WO | WO 2006/111861 | 10/2006 |
| WO | WO 2006/129196 | 12/2006 |
| WO | WO 2007/026163 | 3/2007 |
| WO | WO 2009/040607 | 4/2009 |
| WO | WO 2010/076569 | 7/2010 |
| WO | WO 2011/101381 | 8/2011 |
| WO | WO 2011/101382 | 8/2011 |

OTHER PUBLICATIONS

International Preliminary Report on Patentability in International Application No. PCT/EP2011/074277, dated Jul. 10, 2013, 5 pages.
International Search Report and Written Opinion in International Application No. PCT/EP2011/074277, dated Feb. 17, 2012, 8 pages.
Japanese Office Action in Patent Application No. 2013-546719, dated Aug. 23, 2016, 3 pages (English translation).

* cited by examiner

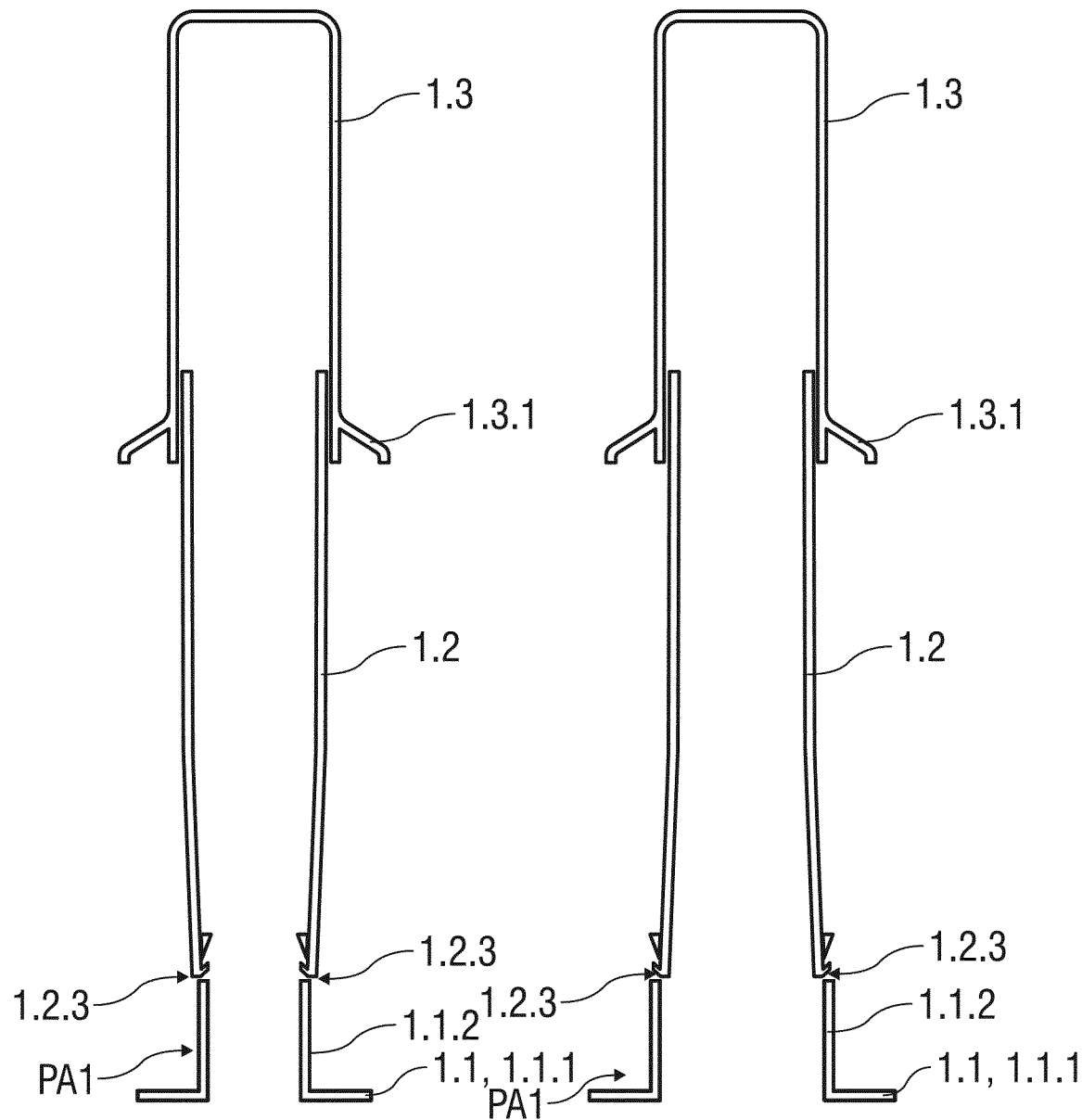

SAFETY DEVICE FOR A PRE-FILLED SYRINGE AND AN INJECTION DEVICE

CROSS REFERENCE TO RELATED APPLICATIONS

The present application is a continuation of U.S. Ser. No. 15/165,624, filed May 26, 2016, which is a continuation of Ser. No. 13/997,370, filed Jun. 24, 2013, which is a National Phase Application pursuant to 35 U.S.C. § 371 of International Application No. PCT/EP2011/074277 filed Dec. 30, 2011, which claims priority to European Patent Application No. 11150080.7 filed Jan. 4, 2011. The entire disclosure contents of these applications are herewith incorporated by reference into the present application.

TECHNICAL FIELD

The present invention relates to safety devices that provide needle safety and more particularly to safety devices for pre-filled syringes. The safety device is adapted to avoid accidental needle pricks and needle injuries before, during and after an injection of a medicament or drug contained in the pre-filled syringe. In particular, the safety device provides needle safety for a subcutaneous self-administrated injection or for an injection administered by a health-care professional. The present invention further relates to injection devices comprising pre-filled syringes.

BACKGROUND

Pre-filled syringes that are filled with a selected dosage of a medicament are well known injection devices for administering the medicament to a patient. Safety devices for covering a needle of a pre-filled syringe before and after use are also well known. Typically, these devices comprise a needle shield that is either manually moved or moved by the action of a relaxing spring to surround the needle.

A different type of safety devices known in the state of the art solves the object of providing needle safety by arranging the pre-filled syringe movable relative to a body, whereas the pre-filled syringe is retracted into the body after the injection.

SUMMARY

Certain aspects of the present invention can provide an improved safety device for a pre-filled syringe.

Certain aspects of the invention can provide an improved injection device comprising a pre-filled syringe that is safe to handle and in particular prevents accidental needle stick injuries.

The aspects can be implemented by a safety device according to the pending claims.

Preferred embodiments of the invention are given in the dependent claims.

In the context of this specification, the terms distal and proximal are defined from the point of view of a person performing an injection. Consequently, a distal direction refers to a direction pointing towards the body of a patient receiving an injection and a distal end defines an end of an element that is directed towards the body of the patient. Respectively, the proximal end of an element or the proximal direction is directed away from the body of the patient receiving the injection and opposite to the distal end or distal direction.

According to the invention, a safety device for a pre-filled syringe with an injection needle comprises
a support body adapted to mount the pre-filled syringe,
a needle shield slidably arranged with respect to the support body,
a retention and locking means for retaining and locking the needle shield with respect to the support body in a first and a second advanced position and in a retracted position.

The needle shield comprises an annular flange adapted to rest on the skin of the patient receiving an injection. The retention and locking means are arranged at a distal end of the safety device.

The needle shield and the support body are arranged so as to telescope with respect to each other between three different positions, namely the first and second advanced position and the retracted position, so as to cover and to expose the injection needle of the pre-filled syringe that may be mounted within the support body of the safety device. Needle safety is provided in at least the second position, so that accidental needle stick injuries may be prevented. In the retracted position, the injection needle is exposed so as to allow tor an insertion of the injection needle into the skin of the patient receiving the injection.

The safety mechanism of the safety device can be viewed as an advancing mechanism that advances the needle shield to the second advanced position after the injection is completed. Alternatively, the safety mechanism may be equivalently described as a retraction mechanism that retracts the injection needle connected to the support body into the needle shield after the injection is completed. The difference between the retraction and the advancing mechanism originates from size of the needle shield relative to the size of the support body. The larger part may be deemed as being static during the telescoping movement of the needle shield and the support body. Thus, a safety device within the scope of the present invention with a relative large support body may be viewed as comprising an advancing mechanism, whereas a safety device within the scope of the present invention with a relative large needle shield may be seen as comprising an retraction mechanism.

The needle shield comprises an annular flange of increased surface that is adapted to rest on the skin of the patient receiving the injection. The needle shield is axially translated between the first advanced position and the retracted position by pushing the safety device against the skin of the patient, whereby the injection needle is inserted into the skin. The safety device is particularly intuitive to operate. Furthermore, the needle shield may be made from an opaque material, so that the injection needle is hidden from the view of the patient. This may help to reduce a possible patient's fear of needles and/or injections.

The arrangement of the retention and locking means at the distal end of the safety device allows for a particularly compact design of the safety device. In particular, the length of the needle shield providing needle safety for the injection needle of the pre-filled syringe retained within and attached to the support body may be minimized. This saves material costs in the manufacturing process of the safety device. The safety device may thus be economically mass-produced. Therefore, the safety device is well suited as a disposable device that is only used in a single injection.

Preferably, the support body, the needle shield and/or the outer body is at least partially made from a transparent plastics material. The support body, the needle shield and/or the outer body may either be completely made from a transparent material or, alternatively, comprise windows or sections that are made from a transparent material. Benefits for having multiple transparent components within the design include aiding visual clarity of contents, reducing the size of the overall visual appearance and adding accuracy to the needle insertion. The retention and locking means are arranged at the distal end of the safety device, so that a view of a user is not obstructed. The content of the pre-filled syringe retained within the support body may be visible at all times. A dose of a medicament or drug is contained in an inner cavity of the pre-filled syringe. The user may visually check the content of the pre-filled syringe throughout the injection.

The needle shield is movable from the first advanced position to the retracted position and further to the second advanced position. The needle shield in the first advanced position protrudes the support body in the distal direction by a first distance. Furthermore, the needle shield in the second advanced position protrudes the support body in the distal direction by a second distance and surrounds the injection needle of the pre-filled syringe after the injection. The first distance is smaller than the second distance to indicate that the safety device has been used.

The retaining and locking means are arranged to releasably retain the needle shield in the first advanced position in a manner that is releasable by a linear translatory movement of the needle shield with respect to the support body parallel to a central axis of the substantially cylindrical safety device. The needle shield is simply pressed against the skin of a patient, whereby the needle shield slides distally and parallel to the central axis towards a retracted position. The distal movement releases the retention of the needle shield in the first advanced position and thus activates the safety mechanism of the safety device that prevents accidental needle stick injuries after the injection.

Preferably, the retention and locking means comprise at least one deflectable resilient arm that provides a simple means for retaining the needle shield in the first advanced position.

According to a possible embodiment of the invention, the resilient arm is arranged with the needle shield as one piece. In particular, the resilient arm may be integrally moulded to the needle shield. The safety device comprises only a few parts preferably made from a plastics material and is inexpensive to manufacture. The resilient arm is arranged within the needle shield so as to prevent the resilient arm and thus the retention of the needle shield in the first, the second and or the retracted position from being influenced from the exterior. This ensures that the safety device works reliably and in particular hinders a person from tampering with the resilient arm locking the needle shield in the second advanced position. Therefore, the safety device is permanently prevented from being re-used after the injection has been carried out.

The needle shield is preferably arranged as a double-walled shield, wherein the resilient arm is integrated to the inner wall to prevent the person from tampering with the resilient arm.

The resilient arm latches to a catching recess formed into a distal end of the support body to releasably retain the needle shield in the first advanced position.

According to another possible embodiment of the invention, the resilient arm is pre-tensioned and deflected in the radial outward direction when latching to the catching recess to releasably retain the needle shield in the first advanced position. The resilient arm is initially stressed and relaxes as soon as the needle shield is pushed with respect to the support body in the distal direction to release the needle shield.

The pre-tensioned resilient arm unbends due to a material memory effect when the needle shield is released from being retained in the first advanced position. In the unstressed state, the resilient arm essentially extends parallel to the central axis of safety device, so that the resilient arm is prevented from engaging the catching recess for a second time. Upon release of the needle shield, the safety mechanism of the safety device is activated. The injection needle is automatically shielded after the injection, whereby a re-use of the safety device and/or the injection device is prevented. Thus, infections resulting from needle stick injuries with contaminated injection needles may be avoided.

According to yet another embodiment, the resilient arm is stressed and inwardly deflected when the needle shield is in the retracted and in the second advanced position. In this embodiment, the resilient arm is initially in an unstressed state and is energized during use of the safety device in an injection. This avoids a malfunctioning of the safety device due to material fatigue after prolonged periods of storage of the safety device.

In particular, the retention and locking means of the safety device may comprise a plurality of resilient arms that reliably retain the needle shield in various positions. According to a possible embodiment of the invention, two of the stressed and inwardly deflected resilient arms are locked to each other by interlocking elements of the retaining and locking means arranged within the needle shield. The safety mechanism of the safety device has a compact design and may further be miniaturized to be used in connection with needle tip safety device that are attached to a hub mounting an injection needle or to a distal tip of a pre-filled syringe.

In another embodiment, the resilient arms are made from a metal material to overcome problems with material fatigue. Furthermore, resilient arms made from the metal material may advantageously be miniaturized to smaller length scales allowing for a compact design of the safety device without compromising reliability.

Two inwardly deflected resilient arms that are arranged opposite to each other may be locked to each other by two interjacent interlocking elements arranged opposite to each other. The two inwardly deflected resilient arms and the two interlocking elements form an interlocked structure that comprises an essentially ring-shaped cross-section. The ring-shaped interlocked structure comprises a reduced diameter that ensures that the released needle shield may move with respect to the support body without getting stuck or jammed. Furthermore, the compact design of this embodiment of the invention allows for a reduction of material and production costs.

The needle shield is biased with respect to the support body in the distal direction by a spring means. The spring means provides an energy source to move the needle shield to the second advanced position. A separate interaction is not required from the user to provide needle safety after the injection has been carried out.

According to yet another embodiment of the invention, the spring means comprises at least one spring arm made from a plastics material. The spring arm provides an alternative spring means that is particularly inexpensive mass-produced. The flexible spring arm is attached to the needle shield and engages a first ramp formed to an outer surface of the support body, whereby the spring arm is deflected and stressed. The deflected and stressed spring arm biases the needle shield in the distal direction. As the spring arm is stored in a unstressed state and is energized during the injection, malfunctions resulting from material fatigue is avoided.

According to the invention, an injection device comprises a safety device and a pre-filled syringe. The safety device comprises
- a support body adapted to mount the pre-filled syringe,
- a needle shield slidably arranged with respect to the support body,
- a retention and locking means for retaining and locking the needle shield with respect to the support body in a first and a second advanced position and in a retracted position.

The retention and locking means are arranged at a distal end of the safety device. The injection device comprising the pre-filled syringe and the safety device combines the aforementioned advantages and avoids inadvertent needle sticks injuries. The injection device is cheap to manufacture and is disposed after a single injection has been carried out.

The injection device is well suited to be used for self-administered injections and for injections performed by a health care professional. Consequently, the person referred to as the patient or the user may be one and the same person.

The pre-filled syringe may be filled with a medicament.

The term "medication", or "drug", or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will be better understood from the detailed description given in the following. The accompanying drawings are given for illustrative purposes only and do not limit the scope of the present invention.

FIGS. 17A to 17D schematically illustrate possible arrangements of a resilient arm retaining the needle shield relative to the support body.

Corresponding parts are marked with the same reference symbols in all figures.

DETAILED DESCRIPTION

Figure 1:
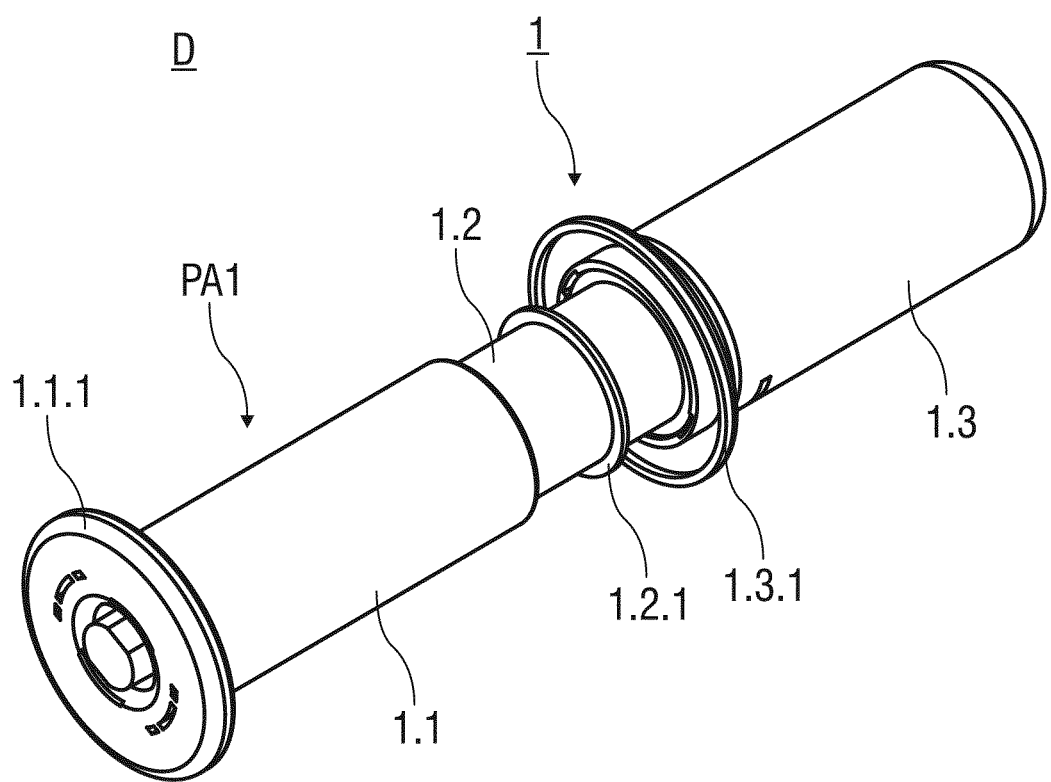
FIG. 1 shows a perspective view of an injection device D according to a first embodiment of the invention before use.

FIG. 1 shows a perspective view of an injection device D with a safety device 1 for a pre-filled syringe 2 according to a first embodiment of the invention. The safety device 1 comprises a substantially cylindrical and hollow needle shield 1.1 with an annular flange 1.1.1 arranged at a distal end thereof. The needle shield 1.1 is arranged as a double walled shield with a substantially inner and outer wall. The annular flange 1.1.1 projects radial outwards from the needle shield 1.1. and is adapted to rest on the skin of the patient during the injection. Edges of the annular flange 1.1.1 are rounded for comfort and to avoid injuries. The needle shield 1.1 is slidably arranged with respect to a support body 1.2 that receives and mounts the pre-filled syringe 2.

Before usage of the safety device 1, the needle shield 1.1 is initially retained in a first advanced position PA1. The needle shield 1.1 in the first advanced position PA1 protrudes the support body 1.2 in a distal direction by a first distance D1.

An annular bearing surface 1.2.1 is formed to the support body 1.2 that protrudes radial outwards. The annular bearing surface 1.2.1 limits the sliding movement of the needle shield 1.1 with respect to the support body 1.2 in the proximal direction.

The safety device 1 comprises an essentially cylindrical and hollow outer body 1.3 with an open distal and a closed proximal end. The proximal end of the support body 1.2 is received within the open distal end of the outer body 1.3. The outer body 1.3 is slidably arranged with respect to the support body 1.2 and may slide in a distal direction to substantially receive the support body 1.2 at the end of an injection stroke.

A circumferential and outwardly protruding support flange 1.3.1 is integrally formed to an outer surface of the outer body 1.3 close to its distal end. The outer body 1.3 is adapted to be gripped and pushed by a user in the distal direction, whereby the support flange 1.3.1 supports the hand of the user performing the injection stroke.

Preferably, the needle shield 1.1, the support body 1.2 and the outer body 1.3 are made from a plastics material. The needle shield 1.1 may be made from an opaque plastics material to hide an injection needle 2.1 of the pre-filled syringe 2 from the view of a patient throughout the injection. This may help to ease a possible fear of needles of the patient. Alternatively, the needle shield 1.1 may be made from a transparent plastics material, so that the user may visually confirm the correct placement of the injection needle 2.1 and easily insert the injection needle 2.1 into the skin of the patient.

According to a possible embodiment of the invention, the support body 1.2 is made from a transparent material, so that the content of the pre-filled syringe 2 received within the support body 1.2 is visible. The safety device 1 comprises retention and locking means M arranged at the distal end of the safety device 1. Thus, the retention and locking means do not obstruct the view of the user checking the content of the pre-filled syringe 2.

Figure 2:
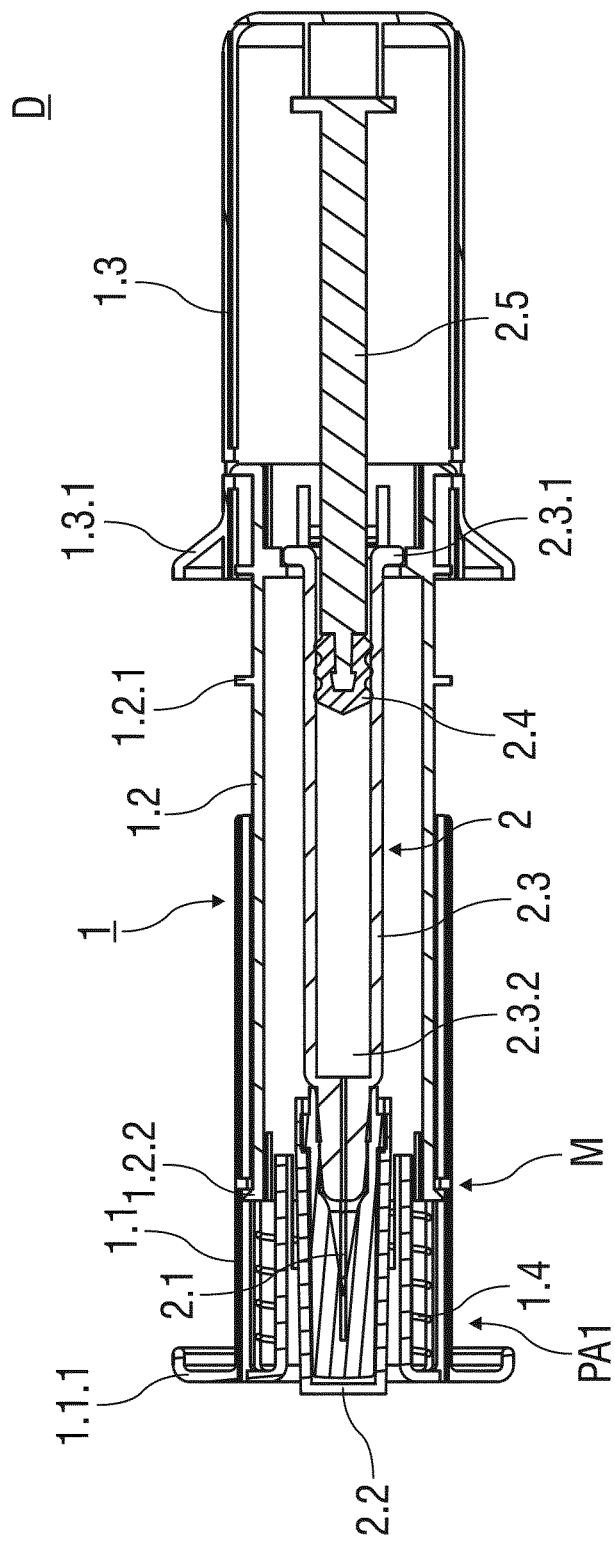
FIG. 2 shows a sectional view of the injection device D according to the first embodiment before use.

FIG. 2 shows a sectional view of the injection device D before use. The injection needle 2.1 of the pre-filled syringe 2 is covered by a needle cap 2.2 that engages a distal tip of a barrel 2.3. Preferably, the needle cap 2.2 is at least partially made from a plastics material like rubber.

The pre-filled syringe 2 inserted into the support body 1.3 and attached thereto by a mechanical connection engages a proximal barrel collar 2.3.1 of the barrel 2.3.

An inner cavity 2.3.2 of the pre-filled syringe 2 contains a dose of a medicament or drug. A stopper 2.4 that is connected to a plunger 2.5 fluid-tightly seals a proximal end of the inner cavity 2.3.2. The stopper 2.4 may be moved by pushing the plunger 2.5 in the distal direction to expel the dose of the medicament through the injection needle 2.1. The plunger 2.5 is attached to or abuts an inner surface of the outer body 1.3, so that the plunger 2.5 and the stopper 2.4 connected thereto may be moved by pushing the outer body 1.3 with respect to the support body 1.2 in the distal direction.

A spring means 1.4 is arranged within the needle shield 1.1 and biases the needle shield 1.1 with respect to the support body 1.2 in the distal direction. According to the first embodiment of the invention, the spring means 1.4 is designed as a compression spring made from a metal. Alternatively, the spring means 1.4 may comprise other suitable means to bias the needle shield 1.1, like, for example, a torsion spring or resiliently deflectable spring arms made from suitable plastics materials.

The retention and locking means M that releasable retain the needle shield 1.1 in the first advanced position PA1 are arranged at the distal end of the safety device 1. The retention and locking means M comprise a catch 1.2.2 formed to an outer surface of the support body 1.2 and protruding therefrom in a radial outward direction to engage the needle shield 1.1.

Figure 3:
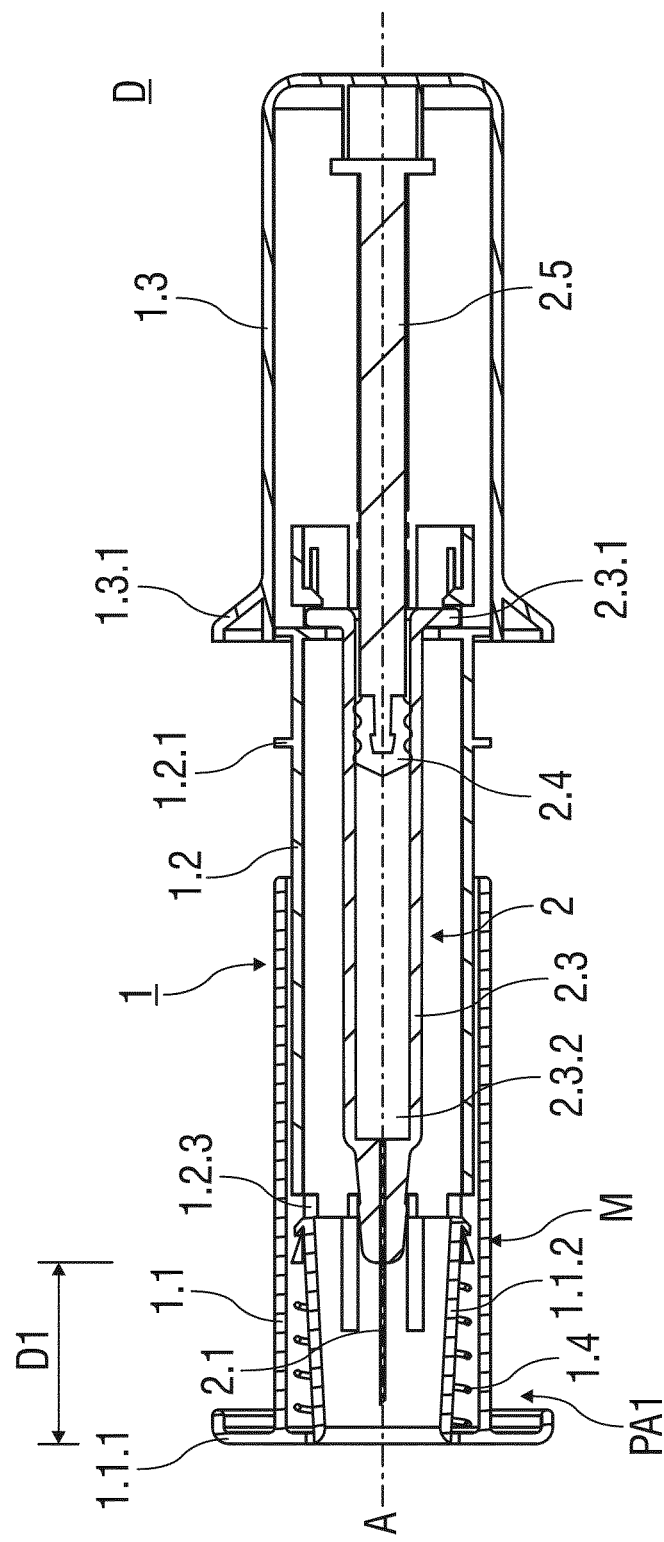
FIG. 3 shows a sectional view of the injection device D according to the first embodiment before a medicament is administered to a patient.

FIG. 3 shows a sectional view of the injection device D after removal of the needle cap 2.2. The retention and locking means M comprise two resilient arms 1.1.2 integrally moulded to the needle shield 1.1 and arranged opposite to each other. The resilient arm 1.1.2 is arranged within the needle shield 1.1 to shield the resilient arm 1.1.2 from exterior influences. In particular, the arrangement of the resilient arm 1.1.2 prevents a person from tampering with the resilient arm 1.1.2 retaining and locking the needle shield 1.1 in various positions. With cross-reference to FIG. 8A, it can be seen that the resilient arms 1.1.2 are radial outwardly deflected and in the pre-tensioned state. The resilient arms 1.1.2 latch to a catching recess 1.2.3 formed into the distal end of the support body 1.2 to releasably retain the needle shield 1.1 in the first advanced position PA1. The mechanical connection between the outwardly flexing resilient arm 1.1.2 and the catching recess 1.2.3 may be released by a linear translatory of movement of the needle shield 1.1 with respect to the support body 1.2 parallel to a central axis A of the substantially cylindrical safety device 1, whereby the deflected resilient arm 1.1.2 unbends due to a material memory effect.

Figure 4:
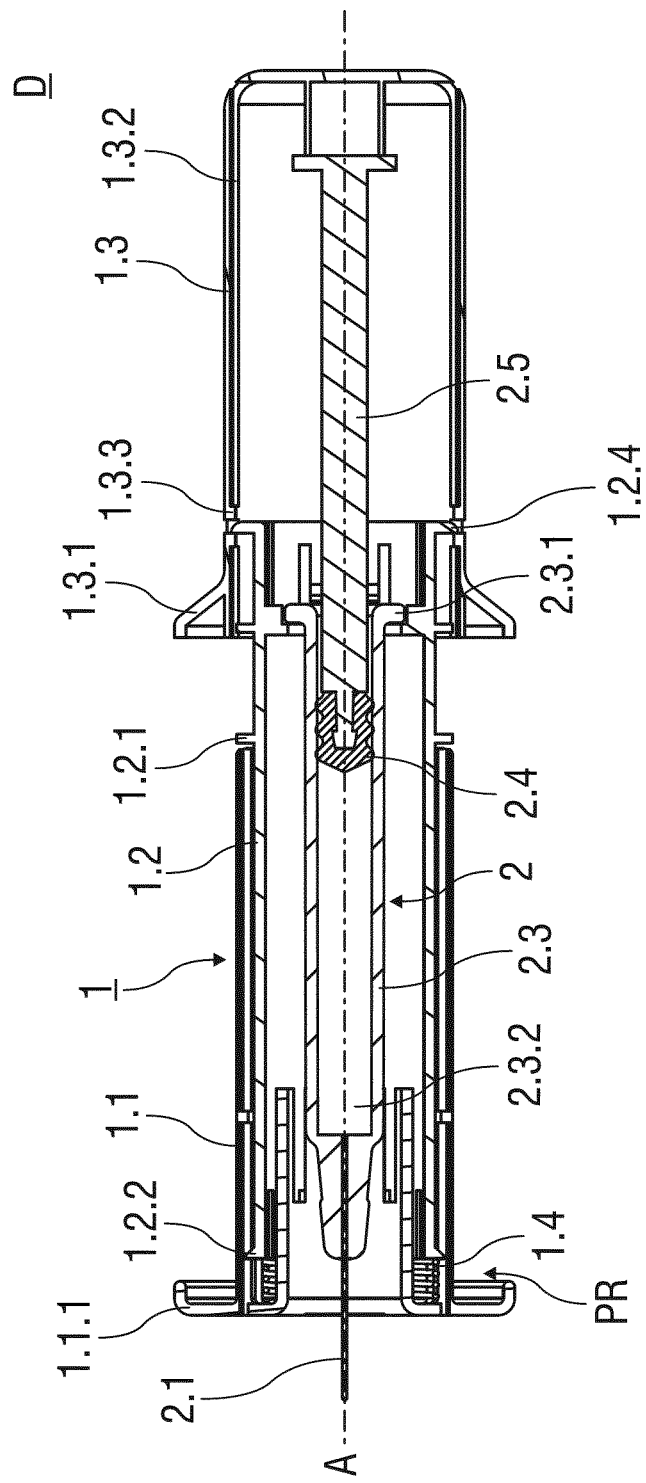
FIG. 4 shows a sectional view of the injection device D according to the first embodiment with a needle shield retracted in a retracted position.

FIG. 4 shows a sectional view of the injection device D before an injection stroke is performed by the user. The needle shield 1.1 is located in a retracted position PR and bears against the annular bearing surface 1.2.1 in the proximal direction. The injection needle 2.1 of the pre-filled syringe 2 protrudes the annular flange 1.1.1 of the needle shield 1.1 in the distal direction. The spring means 1.4 designed as the compression spring is fully compressed and stressed.

An outward projection 1.2.4 is formed to a proximal end of the support body 1.2 that protrudes radial outwards into a longitudinal recess 1.3.2 formed into an inner surface of the outer body 1.3. Preferably, two outward projections 1.2.4 are formed to opposite sides of the support body 1.2 that are received within respective longitudinal recesses 1.3.2 of the outer body. The longitudinal recess 1.3.2 extends parallel to the central axis A and over a substantial axial length of the outer body 1.3. The outward projection 1.2.4 travels within the longitudinal recess 1.3.2 when the outer body 1.3 is slid with respect to the support body 1.2 to expel the dose of the medicament contained in the pre-filled syringe 2 through the injection needle 2.1. This avoids a relative rotation between the outer body 1.3 and the support body 1.2 during the injection, so that a jamming of these parts 1.2, 1.3 may be prevented.

Furthermore, a first inward projection 1.3.3 is located at the distal end of the longitudinal recess 1.3.2 that abuts the outward projection 1.2.4 of the support body 1.2. The outward projection 1.2.4 has to overcome the first inward projection 1.3.3 before the outer body 1.3 may travel with respect to the support body 1.2 in the distal direction. The interaction between the inward and outward projection 1.3.3, 1.2.4 generates a resistive force that is larger than a respective required force required to move the needle shield 1.1 from the first advanced position PA1 to the retracted position PR. This ensures that the needle shield 1.1 is in the retracted position PR and the injection needle 2.1 is inserted into the skin of the patient before the outer body 1.3 is pushed distally. Thus, so-called wet injections and a spilling of the medicament before the injection needle 2.1 is inserted into the skin of the patient are avoided.

Figure 5:
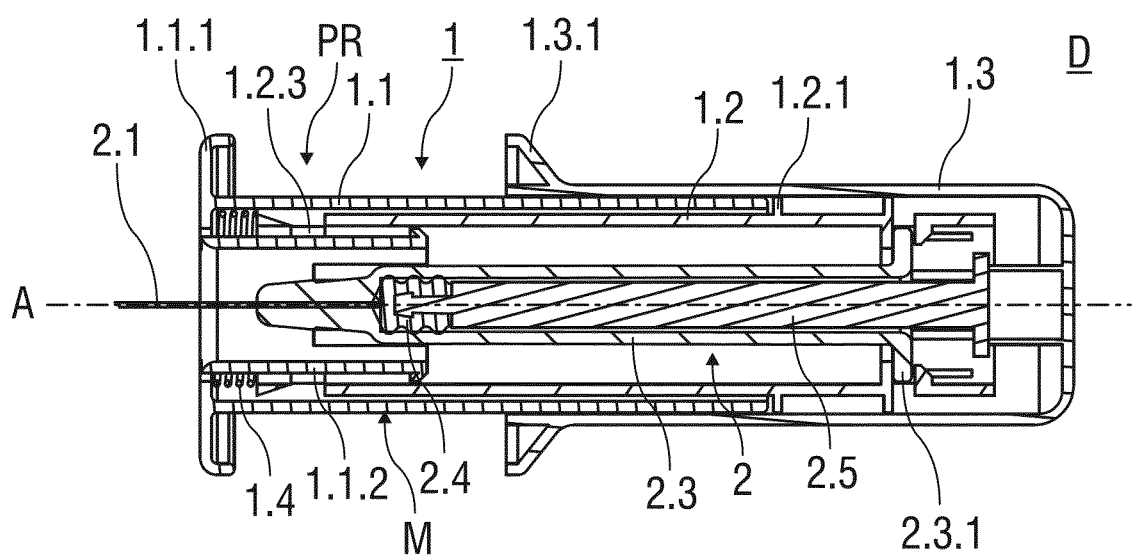
FIG. 5 shows a sectional view of the injection device D according to the first embodiment after a medicament has been administered to the patient.

FIG. 5 shows a sectional view of the injection device D at the end of the injection stroke. The stopper 2.4 connected to the plunger 2.5 is fully depressed into the inner cavity 2.3.1 of the pre-filled syringe 2. The support body 1.2 is substantially received within the hollow outer body 1.3.

The resilient arm 1.1.2 of the retention and locking means M is in a mechanical unstressed state and extends essentially parallel to the central axis A of the safety device 1.

Figure 6A:
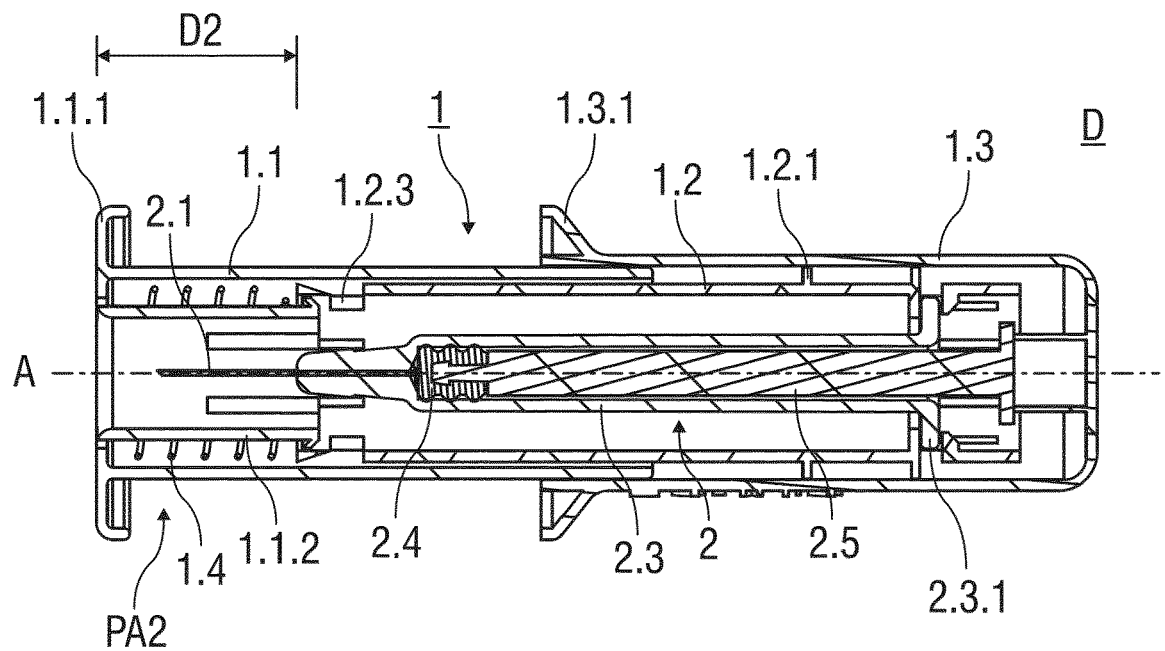
FIGS. 6A and 6B show two different sectional views of the injection device D according to the first embodiment after removal from the injection site.
Figure 6B:
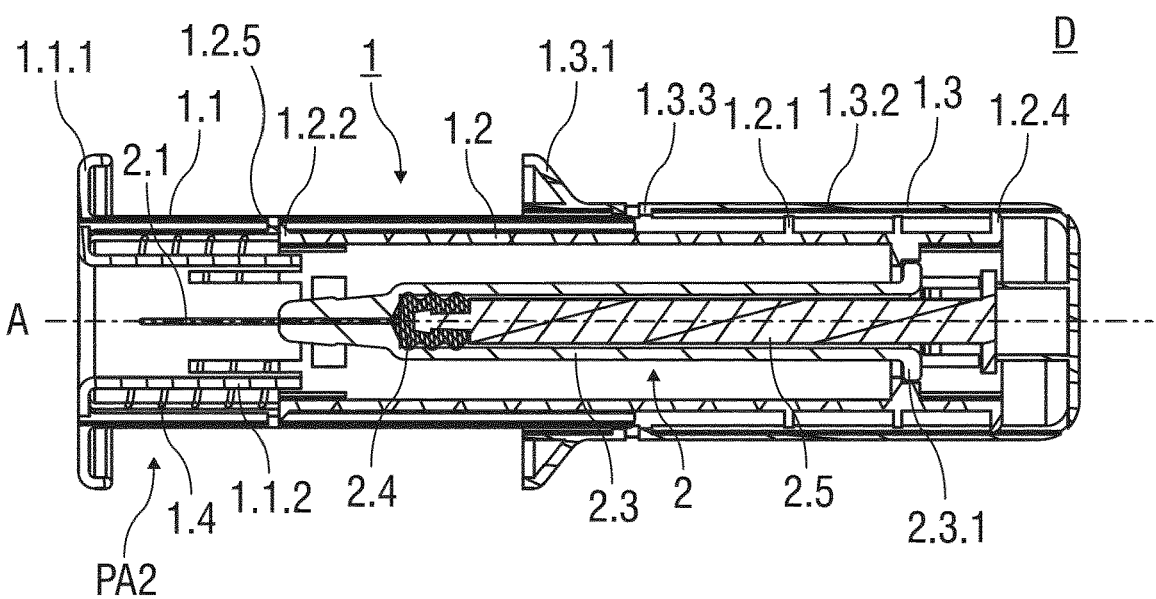

FIGS. 6A and 6B show two different sectional views of the injection device D after removal from the injection site. The sectional plane shown in FIG. 6A extends perpendicularly to the one shown in FIG. 6B. The needle shield 1.1 is located in a second advanced position PA2 and surrounds the injection needle 2.1 after the injection.

As shown in FIG. 6A, the resilient arm 1.1.2 extends parallel to the central axis A, so that a second engagement of the resilient arm 1.1.2 with the catching recess 1.2.3 is avoided. The resilient arm 1.1.2 may thus pass beyond the catching recess 1.2.3, so that the needle shield 1.1 in the second advanced position PA2 protrudes the support body 1.2 by a second distance D2 that exceeds the first distance D1.

The needle shield 1.1 is locked to the second advanced position PA2 so that a subsequent exposure of the injection needle 2.1 is prevented. As shown in FIG. 6B, the catch 1.2.2 of the support body 1.2 abuts a second inward projection 1.2.5 formed to an inner surface of the needle shield 1.1 to prevent a proximal movement of the needle shield 1.1 with respect to the support body 1.2.

Figure 7:
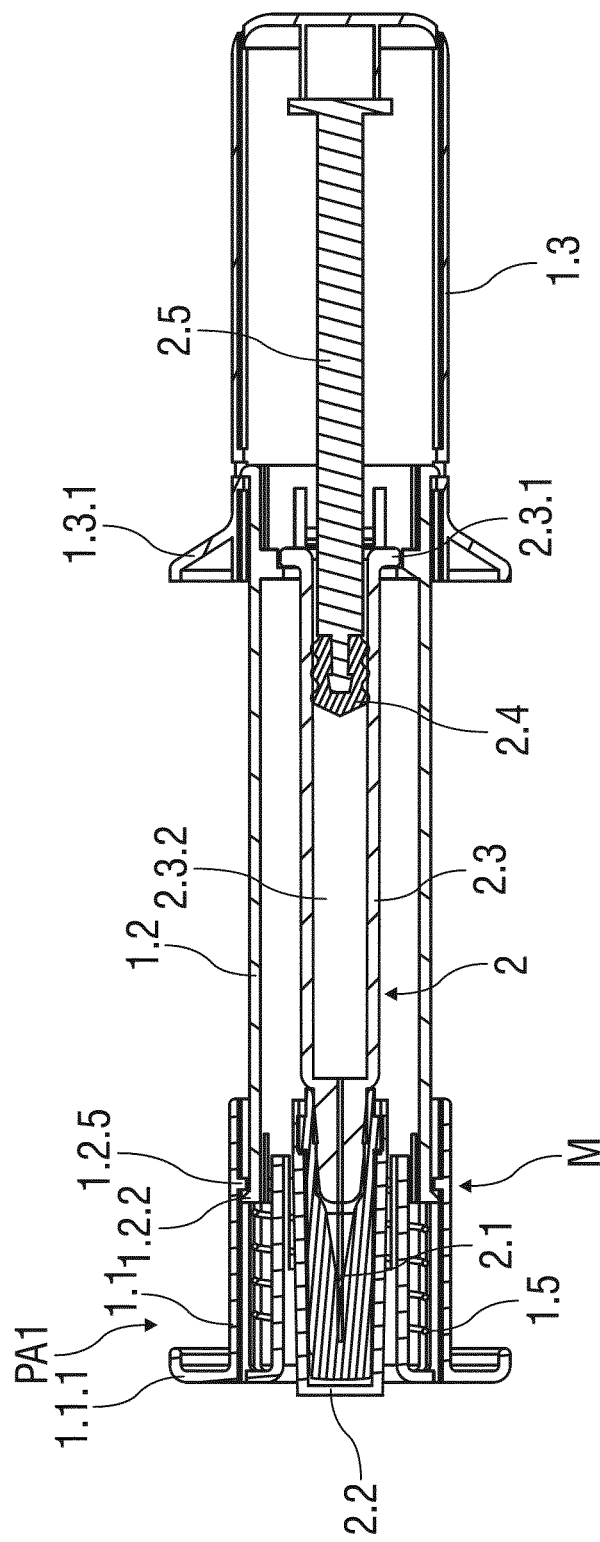
FIG. 7 shows a sectional view of the injection device D according to a second embodiment before use.

FIG. 7 shows a sectional view of an injection device D according to a second embodiment of the invention in a packaged state before the injection device D is used to administer the dose of the medicament contained in the pre-filled syringe 2 to the patient.

The safety device 1 according to the second embodiment of the invention is similar to the one of the first embodiment in both functionality and design. A needle shield 1.1 of the second embodiment comprises compact dimensions and covers, compared to the needle shield 1.1 of the first embodiment, only a relative small area of the support body 1.2 when arranged in the first advanced position PA1, the second advanced position PA2 or the retracted position PR. In particular when the pre-filled syringe 2 is retained in the support body 1.2 made from a transparent material, the user may clearly view the content of the pre-filled syringe 2 independent of the positioning of the needle shield 1.1.

The retention and locking means M of the safety device 1 according to the second embodiment of the invention work similar to the retention and locking means M of the first embodiment described before.

FIG. 8A to 8E illustrate in detail the safety mechanism and the retention and locking means arranged at the distal end of the safety device 1 according to the first and second embodiment of the invention.

Figure 8A:
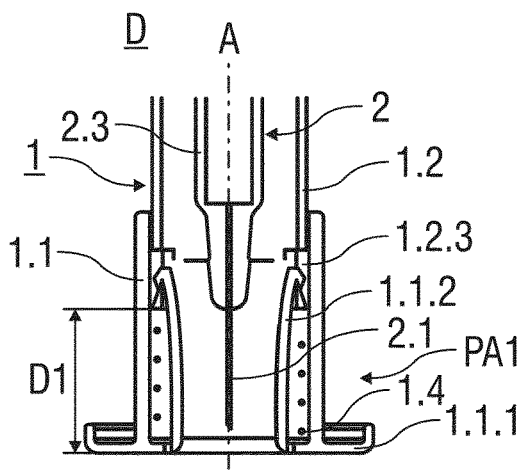
FIG. 8A to 8E illustrate in detail the retention and locking means arranged at the distal end of the safety device 1 according to the first and second embodiment of the invention.
Figure 8B:
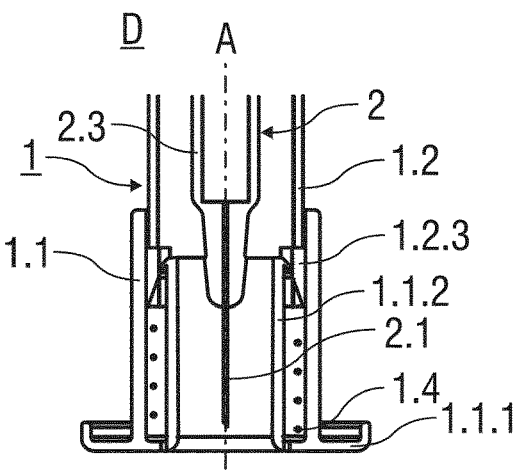

A possible sequence of actions for administering the dose of the medicament to the patient with the injection device D according to the first and second embodiment of the invention is described in the following:

After removal of the needle cap 2.2 from the distal tip of the barrel 2.3, the injection device D is arranged at the injection site, so that the annular flange 1.1.1 rests onto the skin of the patient. The needle shroud 1.1 is retained in the first advanced position PA1, wherein, as illustrated in FIG. 8A, the needle shroud 1.1 projects from the distal end of the support body 1.2 by the first distance D1. The outer body 1.3 is gripped by the user performing the injection and pushed distally towards the skin surface. As a distal movement of the outer body 1.3 with respect to the support body 1.2 is initially prevented by the interaction of outward projection 1.2.4 with the first inward projection 1.3.3, the needle shield 1.1 is released from the first advanced position and pushed in the proximal direction, as illustrated in FIGS. 8A and 8B. The outwardly deflected resilient arms 1.1.2 disengage the catching recesses 1.2.3 and unbend due to a material memory effect. The resilient arm 1.1.2 now extends straight and substantially parallel to the central axis A of the safety device 1.

Figure 8C:
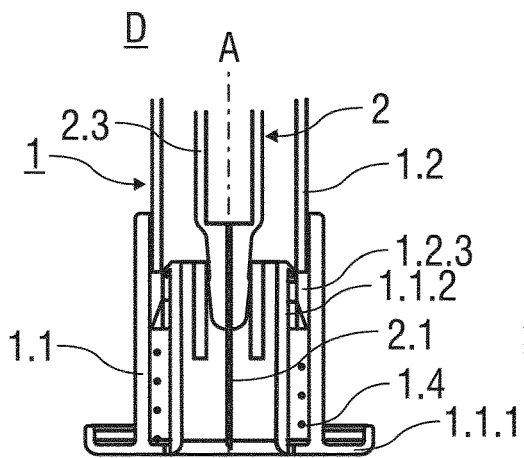
Figure 8D:
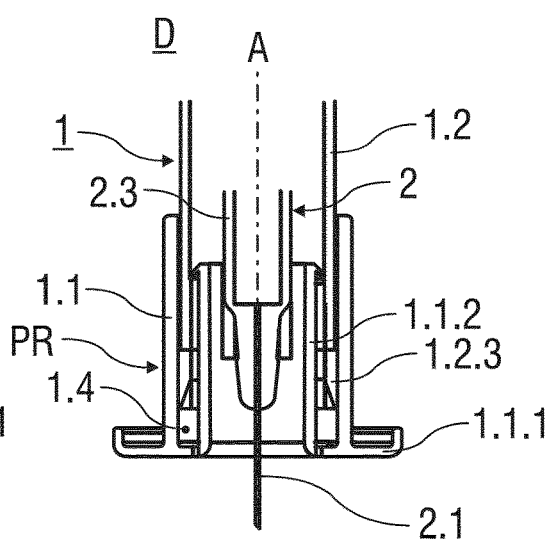
Figure 8E:
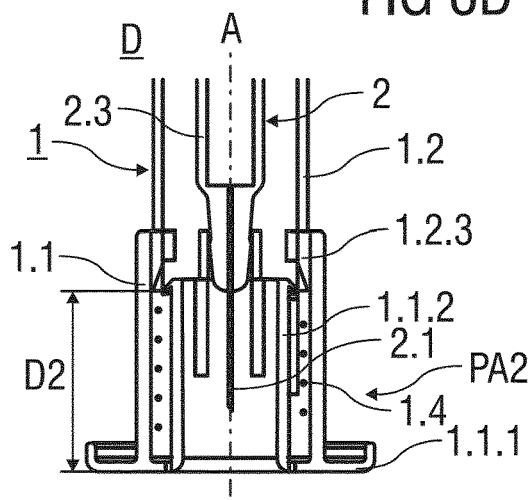

As illustrated in FIG. 8C, the needle shield 1.1 is moved further in the proximal direction towards the retracted position PR shown in FIG. 8D, whereby the injection needle 2.1 is inserted into the skin of the patient.

After the needle shield 1.1 reached the retracted position PR pushing the outer body 1.3 in the distal direction causes the outward projection 1.2.4 to overcome the first inward projection 1.3.3, whereby the outer body 1.3 is released, so that the outer body 1.3 may move in the distal direction. Simultaneously, the stopper 2.4 connected to the outer body 1.3 via the plunger 2.5 depresses into the inner cavity 2.3.2, whereby the dose of the medicament contained in the inner cavity 2.3.2 is expelled through the injection needle 2.1 and disposed beneath the skin of the patient.

When the stopper 2.4 is fully depressed into the inner cavity 2.3.2, the injection device D is removed from the injection site. The spring means 1.4 relax and move the needle shroud 1.1 to the second advanced position PA2 shown in FIG. 8E. The resilient arm 1.1.2 passes beyond the catching recess 1.2.3, so that the needle shroud 1.1 projects from the support body 1.2 by the second distance D2 that is larger than the first distance D1.

Even if the injection is aborted before the stopper 2.4 reaches the distal end of the inner cavity 2.3.2 and the medicament is only partially administered, needle safety is still provided upon removal of the injection device D from the injection site. The needle shield 1.1 is driven to the second position PA2 shown in FIG. 8E to cover the injection needle 2.1 after the medication has been partially delivered.

Figure 9:
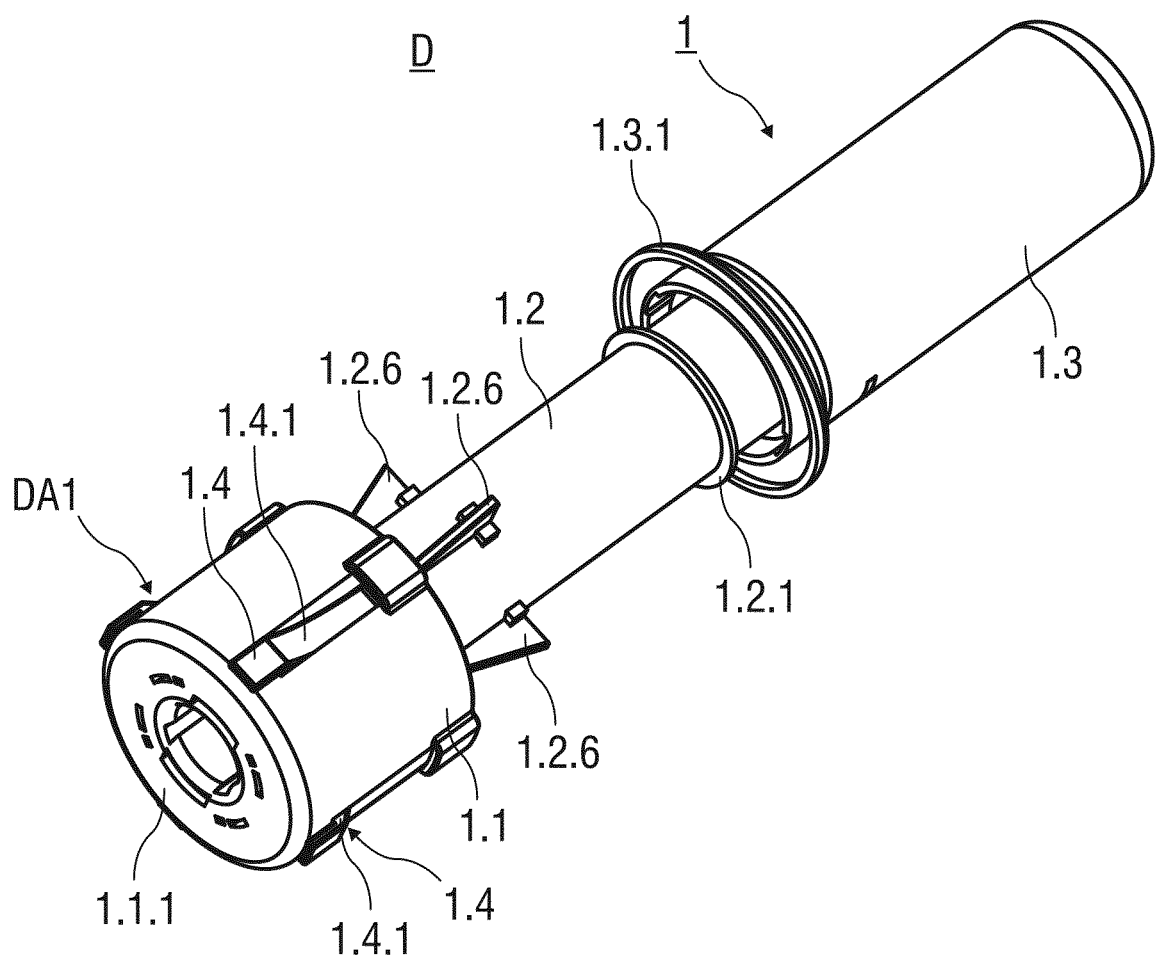
FIG. 9 shows a perspective view of an injection device D according to a third embodiment of the invention before use.

FIG. 9 shows an injection device D according to a third embodiment of the invention in a perspective view before use. The needle shield 1.1 of the third embodiment is biased in the distal direction by spring means 1.4 that comprise a plurality of spring arms 1.4.1 made from a resilient plastics material. A plurality of longitudinal apertures 1.1.3 corresponding to the spring arms 1.4.1 are formed into the needle shield 1.1. The longitudinal aperture 1.1.3 allows for a deflection of the spring arm 1.4.1 in the radial outward direction.

Figure 10:
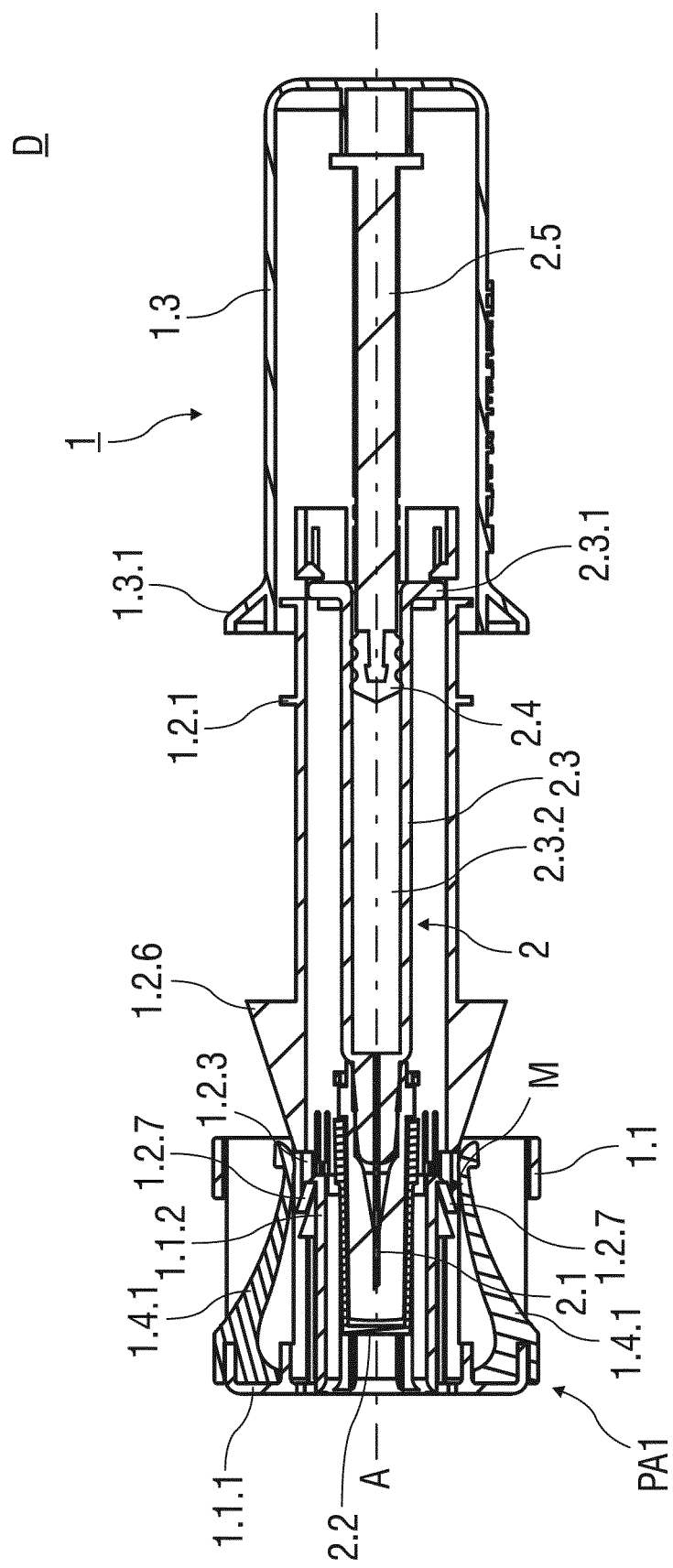
FIG. 10 shows a sectional view of the injection device D according to the third embodiment before use.

FIG. 10 shows a sectional view of the injection device D according to the third embodiment before use. The spring arms 1.4.1 are attached to a distal end of the needle shield 1.1. A proximal end of the spring arm 1.4.1 engages a first ramp 1.2.6 formed to the outer surface of the support body 1.2. During the injection, the proximal end of the spring arm 1.4.1 travels along the first ramp 1.2.6, whereby the spring arm 1.4.1 is deflected outwardly and stressed to bias the needle shield 1.1 with respect to the support body 1.2 in the distal direction.

The resilient arm 1.1.2 of the retention and locking means M latches to the catching recess 1.2.3 to releasably retain the needle shield 1.1 in the first advanced position PA1. The resilient arm 1.1.2 is not pre-tensioned and extends essentially parallel to the central axis A of the safety device 1. A second ramp 1.2.7 is formed to the distal end of the support body 1.2 that engages and deflects the resilient arm 1.1.2 in the radial inward direction when the needle shield 1.1 is displaced with respect to the support body 1.2 in the proximal direction, whereby the resilient arm 1.1.2 disengages the catching recess 1.2.3 to release the needle shield 1.1.

Figure 11A:
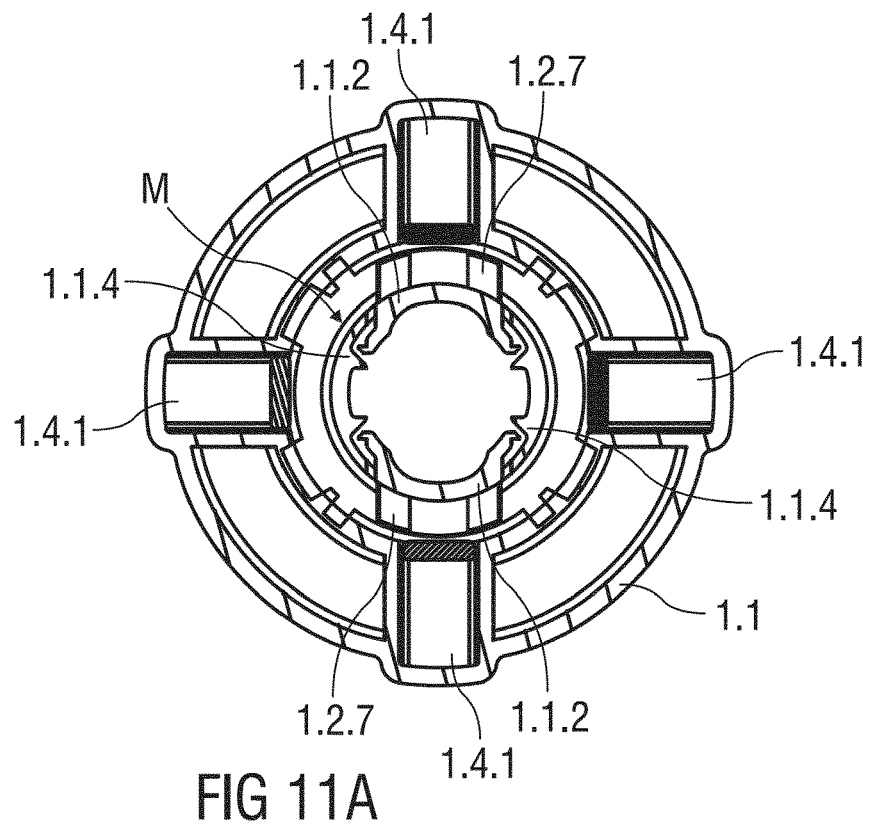
FIGS. 11A and 11B show two cross-sections of the needle shield 1.1 according to third embodiment of the invention.
Figure 11B:
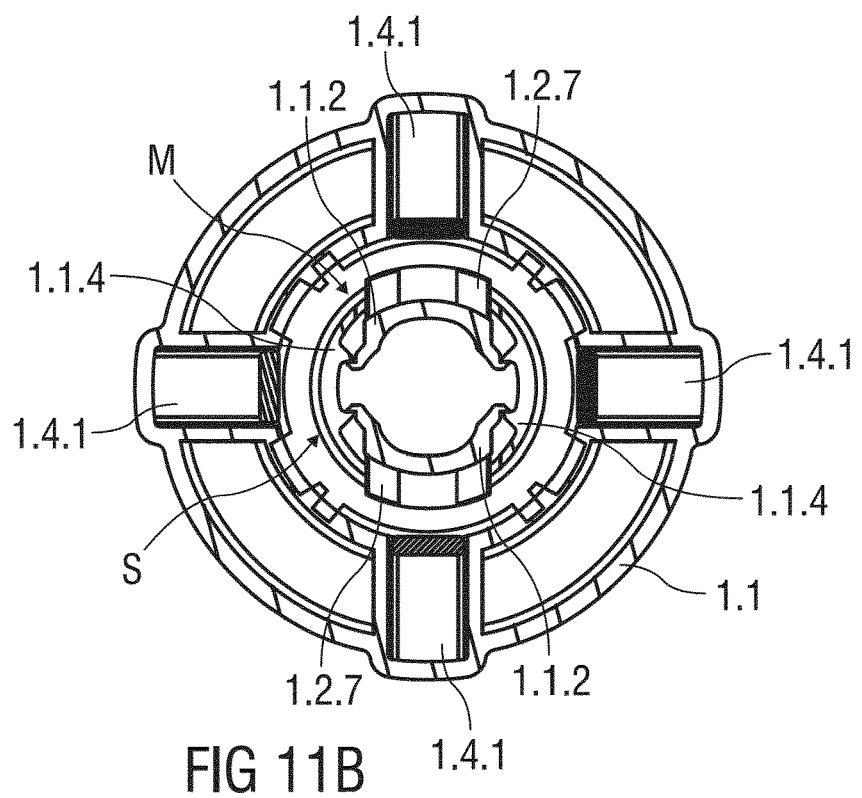

FIGS. 11A and 11B show two cross-sections of the needle shield 1.1 according to third embodiment of the invention. The sectional views shown in FIGS. 11A and 11B extend perpendicular to the central axis A of the safety device 1.

As can be seen in FIG. 11A, the retention and locking means M comprise two resilient arms 1.1.2 arranged opposite each other. The resilient arms 1.1.2 are in a mechanically unstressed state and latch to the catching recess 1.2.3. According to the third embodiment, the retention and locking means M comprises two interlocking elements 1.1.4 respectively arranged in the area between the two resilient arms 1.1.2.

The interlocking elements 1.1.4 are arranged opposite to each other and act as means to lock the two resilient arms 1.1.2 to each other when the resilient arms 1.1.2 are deflected in the radial inward direction after the resilient arms 1.1.2 engaged the second ramp 1.2.7, as illustrated in FIG. 11B. The inwardly deflected and stressed resilient arms 1.1.2 latch to the interjacent interlocking elements 1.1.4, so that the deflected resilient arms 1.1.2 are retained in an inwardly deflected position and locked together. The two interlocking elements 1.1.4 and the two resilient arms 1.1.2 form an essentially ring-shaped interlocked structure S.

Figure 12:
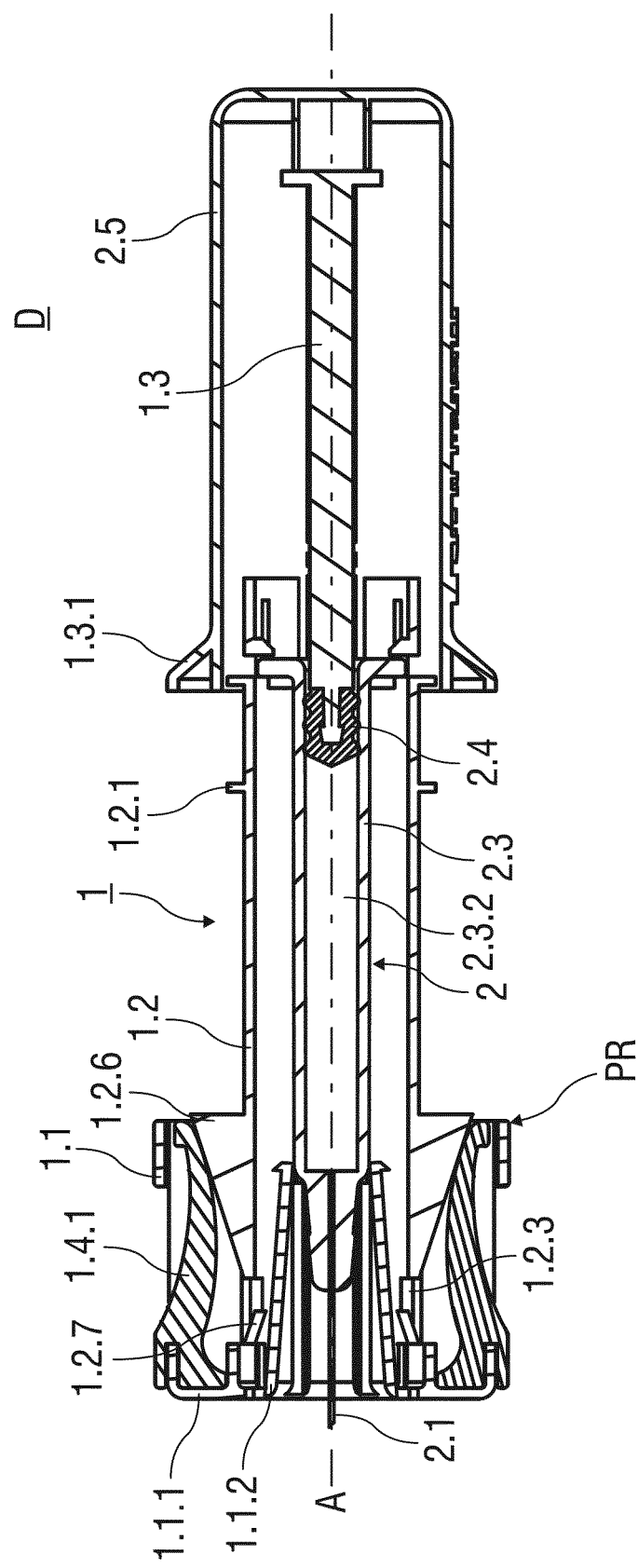
FIG. 12 shows a sectional view of the injection device D according to the third embodiment before the medicament is administered to a patient.

FIG. 12 shows a sectional view of the injection device D according to the third embodiment of the invention with the needle shield 1.1 positioned in the retracted position PR.

The spring arm 1.4.1 engages the first ramp 1.2.6 and is deflected in the radial outward direction. The spring arm 1.4.1 is stressed and biases the needle shield 1.1 in the distal direction.

The resilient arm 1.1.2 engages the second ramp 1.1.2 arranged at the distal end of the support body 1.2. The second ramp 1.2.7 pushes the resilient arm 1.1.2 radial inwardly, so that the deflected resilient arm 1.1.2 is oriented with respect to the central axis A at an acute angle.

Figure 13:
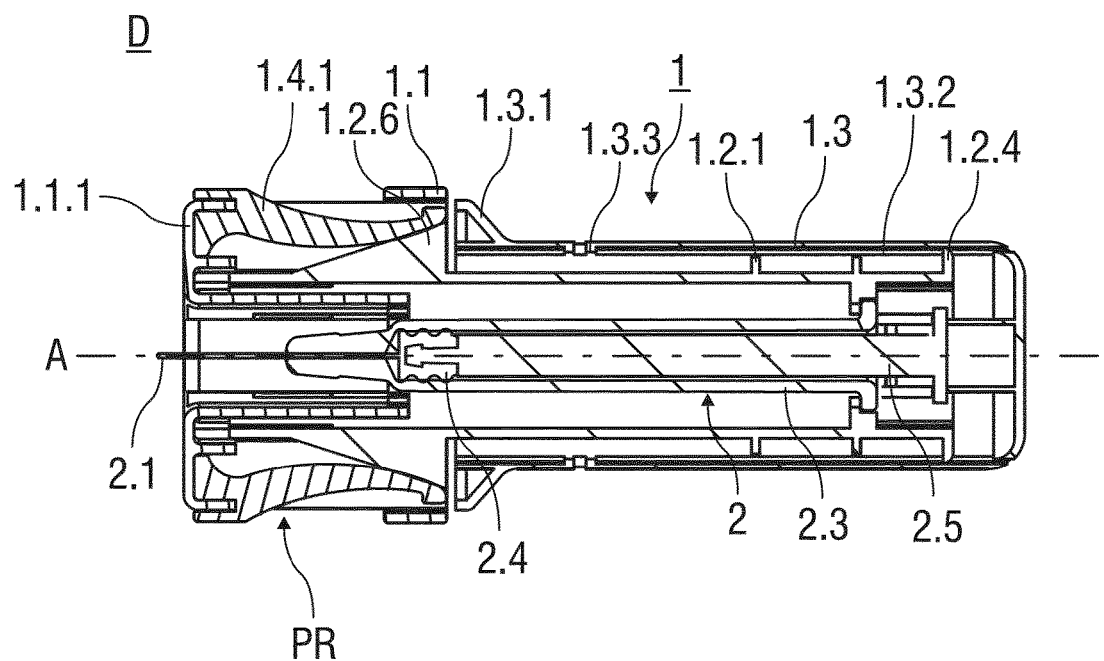
FIG. 13 shows the injection device D according to the third embodiment after a medicament has been administered to the patient.

FIG. 13 shows the injection device D according to third embodiment of the invention after the dose of the medicament contained in the inner cavity 2.3.2 of the pre-filled syringe 2 has been administered to the patient. The support body 1.2 is substantially received within the outer body 1.3 and the stopper 2.4 is fully depressed in the inner cavity 2.3.2.

Figure 14:
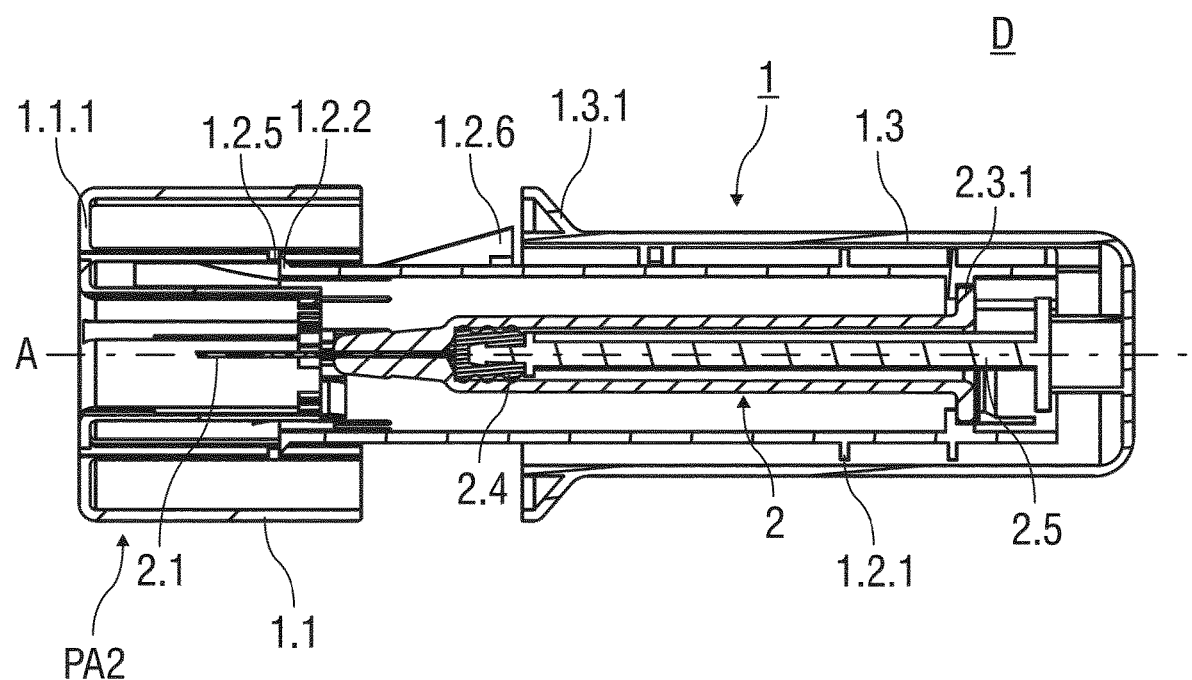
FIG. 14 shows the injection device D according to the third embodiment in a needle safe state.

FIG. 14 shows the injection device D according to the third embodiment of the invention in the needle safe state. The needle shield 1.1 is locked to the second advanced position PA2 and surrounds the injection needle 2.1 to prevent accidental needle stick injuries.

The catch 1.2.2 formed to the distal end of the support body 1.2 latches to the second inward projection 1.2.5 connected to the needle shield 1.1 to permanently lock the needle shield 1.1 to the second advanced position PA2, so that a re-exposure of the injection needle 2.1 is prevented.

Figure 15:
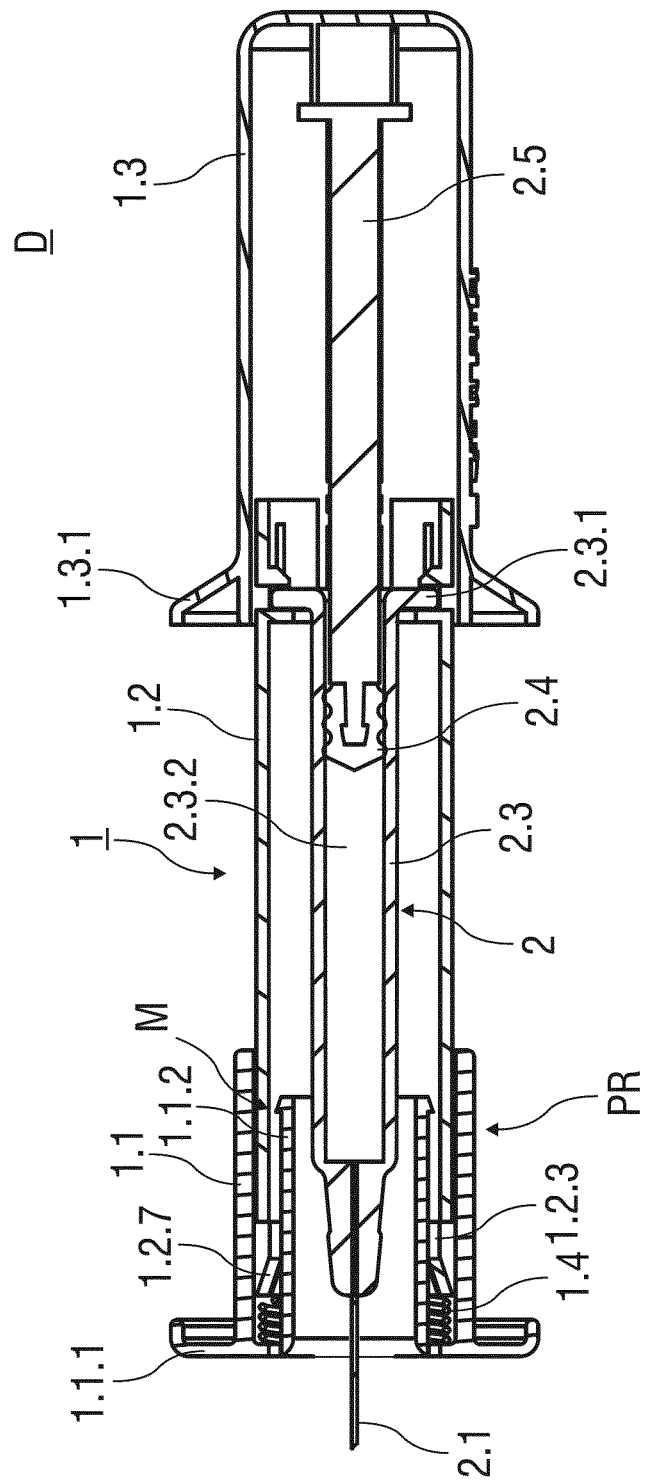
FIG. 15 shows a sectional view of an injection device D according to a forth embodiment of the invention with the needle shield retained in the retracted position.

FIG. 15 shows a sectional view of an injection device D according to a forth embodiment of the invention. The forth embodiment represents one of many possible examples of injection devices D that are within the scope of the present invention and can be viewed as a particularly advantageous combination of the second and the third embodiment already described herein above.

In particular, the injection device D according to the forth embodiment is similar in outer appearance to the injection device D of the second embodiment and comprises the needle shield 1.1 of particular compact design. The retaining and locking means M are designed similar to the injection device D of the third embodiment and comprise two inwardly deflectable resilient arms 1.1.2 that may be locked to each other via interjacent locking elements 1.1.4 to form the interlocked structure S with essentially ring-shaped cross-section as illustrated in detail in FIGS. 11A and 11B.

The injection device D according to the third and forth embodiment of the invention is essentially used during an injection as described herein above. In particular, a possible sequence of actions include the removal of the needle cap 2.2 from the distal tip of the barrel 2.3, the arrangement of the injection device D at the injection site in manner, so that the annular flange 1.1.1 rests onto the skin of the patient, gripping the outer body 1.3 and pushing the outer body 1.3 towards the skin surface, whereby the needle shroud 1.1 first moves from the first advanced position PA1 to the retracted position PR before the outer body 1.3 is translated in the distal direction to inject the dose of the medicament. After the injection device D is taken away from the injection site, the spring means 1.4 relaxes and moves to the second advanced position PA2.

FIGS. 16A to 16D illustrate in detail the retention and locking means M according to the third and forth embodiment of the invention.

Figure 16A:
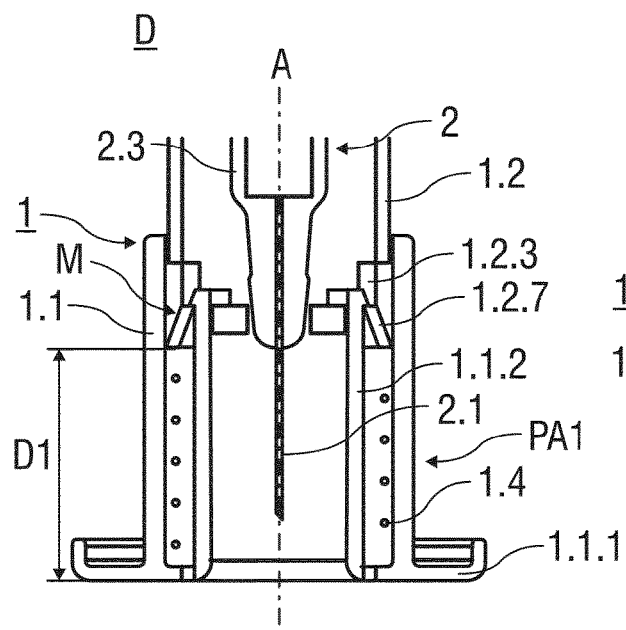
FIGS. 16A to 16D illustrate in detail the retention and locking means according to the third and forth embodiment of the invention.
Figure 16B:
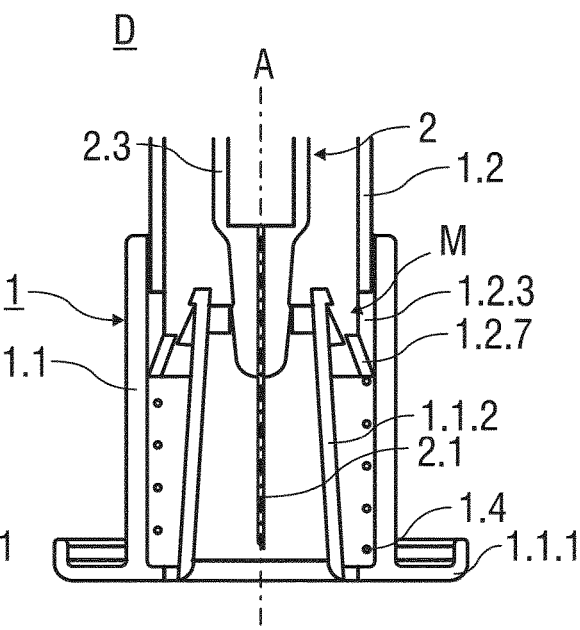

Before the injection, the needle shield 1.1 is initially retained in the first advanced position PA1 shown in FIG. 16A. The needle shield 1.1 is releasably retained in the first advanced position PA1 by the retaining arm 1.1.2 engaging the catching recess 1.2.3, wherein the retaining arm 1.1.2 is not mechanically stressed and extends essentially parallel to the central axis A. The needle shield 1.1 is released by a linear translation parallel to the central axis A in the proximal direction, whereby the second ramp 1.2.7 abuts and deflects the resilient arm 1.1.2 in the radial inward direction, as illustrated in FIG. 16B. The two deflected resilient arms 1.1.2 latch to the interlocking elements 1.1.4 to form the interlocked structure S as illustrated in FIG. 11B.

Figure 16C:
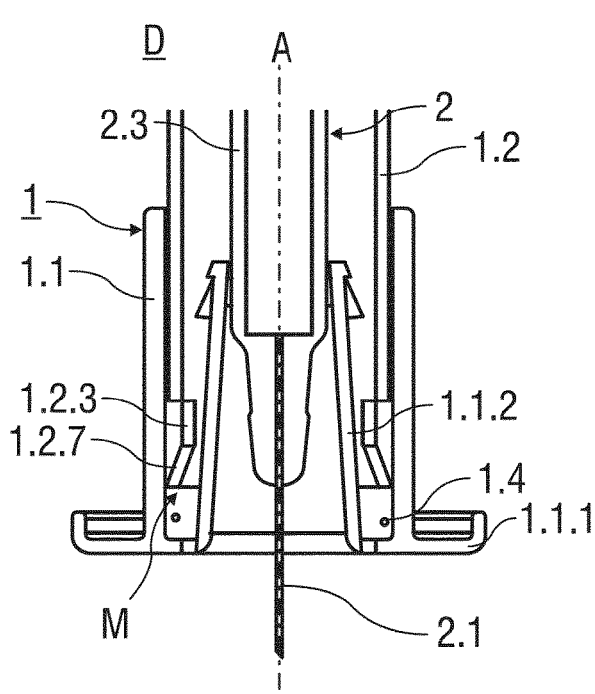
Figure 16D:
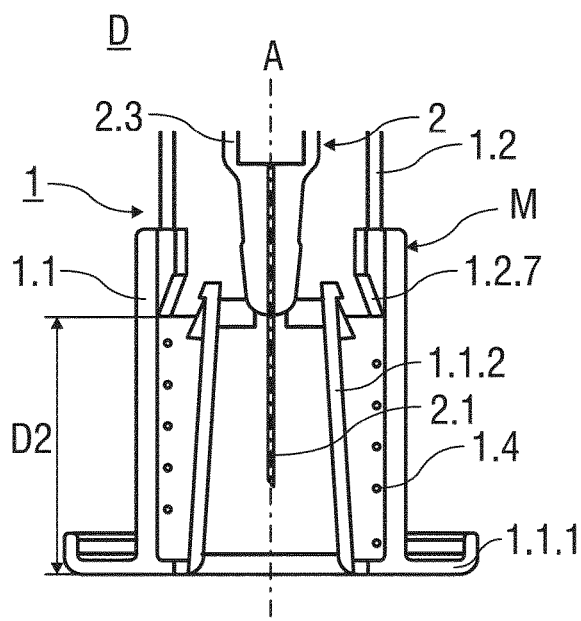

During the injection, the needle shield 1.1 moves further in the proximal direction until the needle shield 1.1 reaches the retracted position PR shown in FIG. 16C. The injection needle 2.1 protrudes the annular flange 1.1.1 resting on the skin of the patient and punctures the skin of the patient. After the dose of the medicament is disposed beneath the skin of the patient, the injection device is removed from the skin. The spring means 1.4 relaxes and pushes the needle shield 1.1 distally to surround the used injection needle 2.1 in the second advanced position PA2. The needle shield 1.1 is permanently locked to the advanced position PA2 to prevent needle stick injuries after use of the injection device D.

FIGS. 17A to 17D illustrate possible arrangements of a resilient arm 1.2.3 retaining the needle shield 1.1 relative to the support body 1.2 within the scope of the present invention.

Figures 17A, 17B:
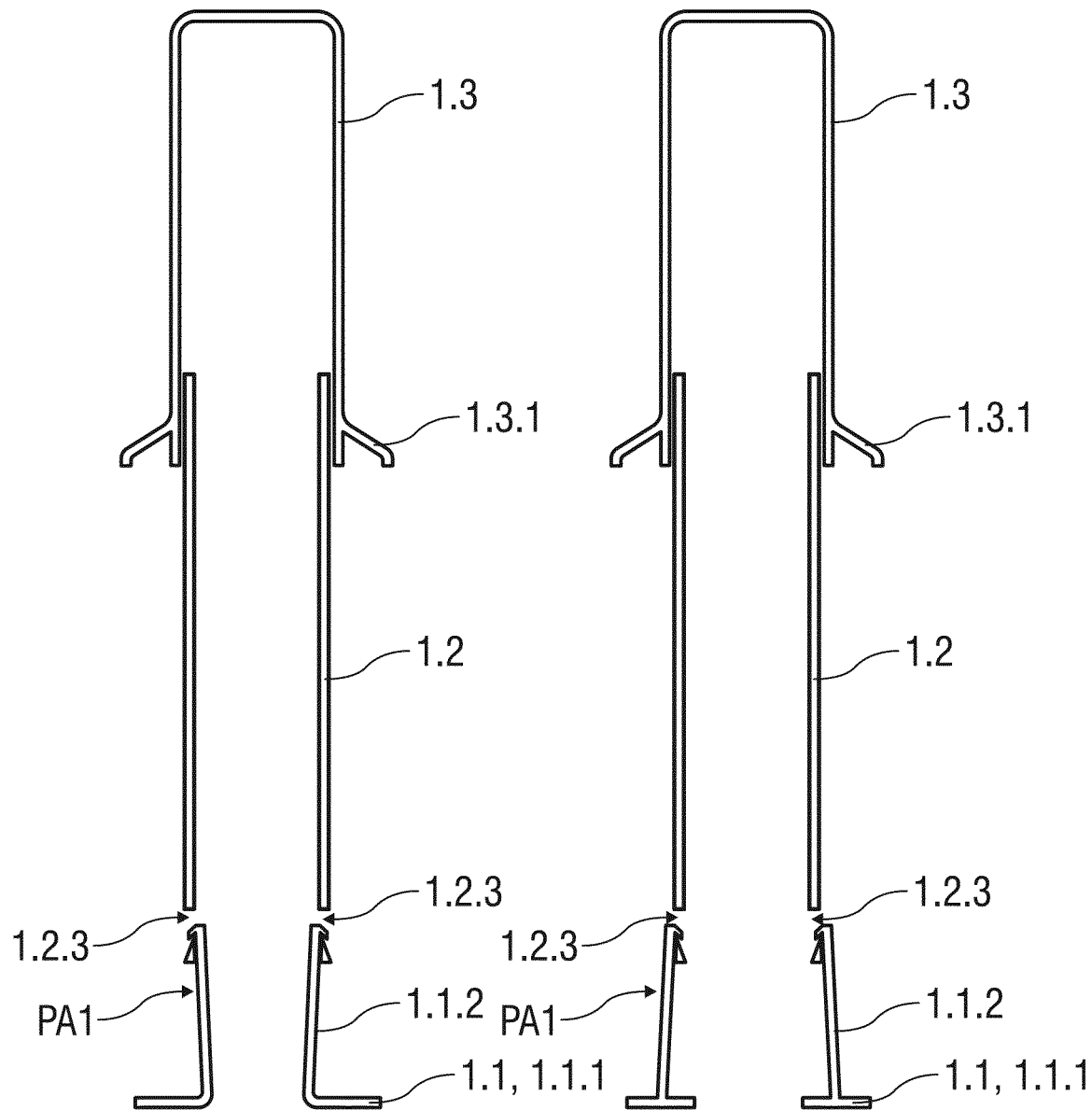

FIG. 17B shows an arrangement of the resilient arm 1.1.2 formed to the needle shield 1.1. The resilient arm 1.1.2 is deflected in the radial inward direction to latch to the catching recess 1.2.3 formed into the distal end of the support body 1.1, so that the needle shield 1.1 is initially retained in the first advanced position PA1.

FIG. 17C shows an arrangement of the resilient arm 1.1.2 formed to the distal end of the support body 1.2. The resilient arm 1.1.2 is deflected in the radial inward direction to latch to the catching recess 1.2.3 formed into the needle shield 1.1, so that the needle shield 1.1 is initially retained in the first advanced position PA1.

FIG. 17D shows an arrangement of the resilient arm 1.1.2 formed to the distal end of the support body 1.2. The resilient arm 1.1.2 is deflected in the radial outward direction to latch to the catching recess 1.2.3 formed the needle shield 1.1, so that the needle shield 1.1 is initially retained in the first advanced position PA1.

The invention claimed is:

1. A safety device for a pre-filled syringe with an injection needle, comprising:
    a body configured to receive the pre-filled syringe;
    a needle shield having a distal annular flange and being slidably arranged along a central axis with respect to the body, wherein the needle shield is releasably retained along the central axis relative to the body in a first position and fixed along the central axis relative to the body in a second position,
    wherein the needle shield in the first position extends from a distal surface of the body by a first distance and the needle shield in the second position extends from the distal surface of the body by a second distance, wherein the first distance is smaller than the second distance; and
    a retention and locking mechanism comprising at least two deflectable resilient arms arranged opposite to each other, the retention and locking mechanism configured to releasably retain the needle shield with respect to the body in the first position and lock the needle shield with respect to the body in the second position.

2. The safety device according to claim 1, wherein the needle shield in the first position protrudes from the body in a distal direction by the first distance and the needle shield in the second position protrudes from the body in the distal direction by the second distance.

3. The safety device according to claim 1, wherein the retention and locking mechanism is generally arranged distally within the safety device.

4. The safety device according to claim 1, wherein the retention and locking mechanism is configured to release the needle shield from the first position by a linear movement of the needle shield with respect to the body.

5. The safety device according to claim 1, wherein the at least two deflectable resilient arms are arranged with the needle shield as one piece.

6. The safety device according to claim 1, wherein the at least two deflectable resilient arms are configured to latch to a recess formed in a distal region of the body.

7. The safety device according to claim 6, wherein the at least two deflectable resilient arms are configured to latch to the recess to retain the needle shield in the second position.

8. The safety device according to claim 6, wherein the at least two deflectable resilient arms are configured to deflect in a radial inward direction and to subsequently unbend when latching to the recess.

9. The safety device according to claim 1, wherein the at least two deflectable resilient arms are inwardly deflectable resilient arms.

10. The safety device according to claim 1, wherein the needle shield is biased with respect to the body in a distal direction by a spring.

11. The safety device according to claim 10, wherein the spring comprises a distal end which bears against a collar arranged on the needle shield.

12. The safety device according to claim 10, wherein the spring comprises a proximal end which bears against the body.

13. The safety device according to claim 1, wherein the retention and locking mechanism and the needle shield are configured to interact with each other at a distal end of the safety device.

14. The safety device according to claim 13, wherein a portion of the needle shield is supported within the body.

15. The safety device according to claim 14, wherein the portion of the needle shield supported within the body comprises the at least two deflectable resilient arms.

16. The safety device according to claim 1, wherein the retention and locking mechanism comprises a recess arranged at a distal end of the safety device, the recess configured to releasably retain the needle shield at the distal end of the safety device.

17. The safety device according to claim 1, wherein the needle shield is releasably retained in the first position by a connection between at least two deflectable resilient arms and a recess formed in a distal region of the body.

18. The safety device according to claim 1, wherein the safety device is configured such that a distal movement of the body relative to the needle shield releases the retention of the needle shield.

19. The safety device according to claim 1, wherein the needle shield covers an injection needle of the safety device in the first position and in the second position.

20. The safety device according to claim 1, wherein when the needle shield is in the first position, the needle shield is prevented from moving along the central axis relative to the body.

21. An injection device comprising:
a pre-filled syringe; and
a safety device comprising:
a body adapted to mount the pre-filled syringe; and
a needle shield having a distal annular flange and being slidably arranged along a central axis with respect to the body,
wherein the needle shield is releasably retained along the central axis relative to the body in a first position and fixed along the central axis relative to the body in a second position,
wherein the needle shield in the first position extends from a distal surface of the body by a first distance and the needle shield in the second position extends from the distal surface of the body by a second distance, wherein the first distance is smaller than the second distance, and
wherein the needle shield is biased with respect to the body in a distal direction by a spring and the spring comprises a proximal end which bears against the body.

22. The injection device of claim 21, wherein the pre-filled syringe contains a drug containing at least one pharmaceutically active compound.

23. A safety device for a pre-filled syringe with an injection needle, comprising:
a body configured to receive the pre-filled syringe; and
a needle shield having a distal annular flange and being slidably arranged along a central axis with respect to the body, wherein the needle shield is releasably retained along the central axis relative to the body in a first position and fixed along the central axis relative to the body in a second position,
wherein the needle shield in the first position extends from a distal surface of the body by a first distance and the needle shield in the second position extends from the distal surface of the body by a second distance, wherein the first distance is smaller than the second distance, and
wherein the needle shield covers a distal tip of the injection needle of the safety device in the first position and in the second position.

* * * * *